(12) United States Patent
Purdie

(10) Patent No.: US 6,657,076 B1
(45) Date of Patent: Dec. 2, 2003

(54) PROCESS FOR PREPARING METHYLENE BISPHOSPHONIC AND SALTS

(75) Inventor: Mark Purdie, Loughborough (GB)

(73) Assignee: AstraZeneca UK Limited, London (GB)

( * ) Notice: Subject to any disclaimer, the term of this patent is extended or adjusted under 35 U.S.C. 154(b) by 0 days.

(21) Appl. No.: 10/088,177

(22) PCT Filed: Sep. 11, 2000

(86) PCT No.: PCT/GB00/03473

§ 371 (c)(1),
(2), (4) Date: Mar. 14, 2002

(87) PCT Pub. No.: WO01/21629

PCT Pub. Date: Mar. 29, 2001

(30) Foreign Application Priority Data

Sep. 17, 1999 (SE) ............................................. 9903345

(51) Int. Cl.$^7$ .................................................. C07F 9/38
(52) U.S. Cl. ............................................ 562/22; 562/21
(58) Field of Search ................................ 562/8, 20, 21, 562/22

(56) References Cited

U.S. PATENT DOCUMENTS 3,251,907 A * 5/1966 Roy ........................... 558/124
3,422,021 A * 1/1969 Roy ........................... 510/469

FOREIGN PATENT DOCUMENTS

GB 1026366 4/1966
WO WO 91/03480 3/1991

OTHER PUBLICATIONS

CA:96:100047 abs of Molekulyarnaya Biologiya (Moscow) by Rozovskaya et al 15(6) pp 1205–23 1981.*
CA:104:149010 abs of Journal of Organometallic Chemistry by Hutchinsom et al 291(2) pp 145–51 1985.*
CA:106:102549 abs of Ep 200980 Nov. 1986.*
CA:101:152243 abs of Journal of Chem. Soc. Perkin Trans. 1 by Blackburn et al (5) pp 119–25 1984.*
CA:96:143232 Journal of Chem. Soc. Chem. Commun. by Blackburn (22) pp 1188–90 1981.*
The Merck Index 10$^{th}$ edition Windholz editor p. 4678 1983.*

* cited by examiner

*Primary Examiner*—Jean F. Vollano
(74) *Attorney, Agent, or Firm*—Fish & Richardson PC

(57) ABSTRACT

A process for the preparation of salts of substituted or unsubstituted methylene bisphosphonic acids by hydrolysing the corresponding acid ester with hydrochloric acid, removing water from the acid azeotropically prior to addition of an amine or a base to produce the resultant salt in good yield.

13 Claims, No Drawings

PROCESS FOR PREPARING METHYLENE BISPHOSPHONIC AND SALTS

This application is a 371 of PCTGB00/03437, filed Sep. 11, 2000, now WO01/21629.

The present invention relates to an improved process for the preparation of salts, in particular amine salts and sodium salts of methylene bisphosphonic acids of formula I

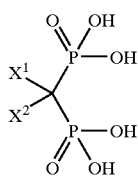

(I)

wherein $X^1$ and $X^2$ are independently hydrogen or halogen. The invention also relates to the salts of methylene bisphosphonic acids of formula I. These salts are useful in the preparation of the compounds described in EP0683789.

Previously known processes for preparing bisphosphonic acids involved hydrolysing the corresponding tetraesters using strong acids, such as halogen acids. Thus, for example, the isopropyl tetraester has been boiled for several hours with concentrated hydrochloric acid. The publication Houben-Weyl, Methoden der Organischen Chemie, XII. 1,352–356 describes the hydrolysis of tetraesters with half-concentrated hydrochloric acid under elevated pressure and at 130–145° C. The disadvantage of these processes is the impurities in the products and the numerous purification steps needed to remove by-products and excess acid.

EP0200980 describes a process in which methylene bisphosphonic acids were prepared by hydrolysing tetraesters with water, by boiling at reflux temperature of the reaction mixture. Whilst problems of impurities of corrosion were largely overcome, the reaction time was very long, as long as 16 hours, which is disadvantageous for commercial production.

The hydrolysis of the tetraester disclosed in WO91/103480 is performed using from 1.0 to 5% by weight hydrochloric acid. Active charcoal is required to decolourise the solution.

GB 1026366 describes the preparation of the tetrasodium salt of dichloromethylenebisphosphonic acid by refluxing dichloromethylene bisphosphonate tetraisopropyl ester with concentrated hydrochloric acid. The acidic solution was concentrated and twice azeotroped with isopropanol. Neutralisation of the acid with sodium hydroxide yielded the tetrasodium salt.

It has now been found that the salt formed from the acid which in turn is formed by hydrolysing a substituted or unsubstituted ester of methylene bisphosphonic acid with 15 to 20% by weight hydrochloric acid, followed by the azeotropic removal of water using n-butanol, can be easily isolated in a good yield and has far fewer impurities.

According to a first aspect of the invention there is provided a process for preparing salts of substituted or unsubstituted methylene bisphosphonic acids of general formula I,

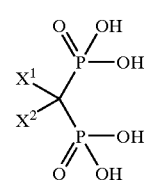

(I)

wherein $X^1$ and $X^2$ are independently hydrogen or halogen, which process comprises hydrolysing, using hydrochloric acid, the corresponding ester of formula II,

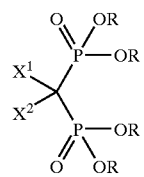

(II)

wherein $X^1$ and $X^2$ are defined above and R is a $C_{1-4}$ straight or branched alkyl group and converting the acid to a salt by reaction with a base characterised in that the concentration of hydrochloric acid is from 15% to 20% by weight, and water is removed azeotropically from the resultant acid using n-butanol prior to the addition of an amine or a base.

Preferably $X^1$ and $X^2$ are both fluorine, chlorine or bromine.

Most preferably $X^1$ and $X^2$ are both chlorine.

The tetraester of formula II is preferably the isopropyl ester such as dichloromethylene bisphosphonate tetraisopropyl ester.

The acid product of the hydrolysis may be reacted with an organic or inorganic base such as a $C_{1-6}$ straight or branched primary, secondary or tertiary alkylamine, aralkyl amine. basic N-containing heterocycle, alkali or alkaline earth metal hydroxides.

The preferred bases are $C_{1-4}$ straight or branched and primary, secondary or tertiary alkyl amines, aralkyl amines, basic N-containing heterocycle, or alkali metal hydroxides.

Suitable bases may be selected from the group comprising triethylamine, tri-n-propylamine, diisopropylethylamine, tri-n-butylamine, pyridine, tribenzylamine and sodium hydroxide.

The volume of hydrochloric acid used is from 3 to 5 volumes and the hydrolysis using the acid is preferably carried out at a temperature of about 80° C. to about 90° C. Following the addition of n-butanol a vacuum is suitably applied.

Thus in a preferred process according to the invention an ester of methylenebisphosphonic acid, such as dichloromethylene bisphosphonate tetraisopropyl ester, is dissolved in from about 15% to about 20% hydrochloric acid, preferably about 18% hydrochloric acid. The resultant solution is added dropwise to a stirred solution of 15% to 18% hydrochloric acid which has been heated to a temperature of from about 80° C. to about 90° C., preferably about 85° C. The total volume of acid used is in the range of from about 3 to about 5 volumes, preferably about 4 volumes. The solution is then stirred at the elevated temperature for from about 1 to about 3 hours, preferably about 2 hours, under a flow of nitrogen, whilst collecting the distillate. After this time the solution is heated to get a steady flow of distillate. Further water is added to the hot reaction mixture and then further solvent removed by distillation.

The reaction mixture is then cooled prior to the addition of n-butanol. Vacuum and heat are then applied to the vessel. Distillate is removed whilst periodically adding n-butanol. An n-butanol solution of the dichloromethylene bisphosphonic acid is then obtained. The solution may then be diluted with n-butanol and another alcohol if desired. To this solution is added the amine or base and the reaction mixture is stirred. For the mono(tri-n-butylamine)salt crystallisation typically begins within 30 minutes, while many others precipitate more rapidly. The suspension is then filtered and the solid washed with n-butanol. The damp solid is dried in vacuo to give the dichloromethylene bisphosphonic acid salt in high yield.

Use of hydrochloric acid within the defined range of concentration in the process of the invention has the advantage that the hydrolysis can be completed within 2 hours. No analytical method is required to follow the reaction and no purification with for example charcoal, is required.

The azeotropic removal of water using n-butanol results in a far superior removal of water than isopropanol. It also has the advantage of producing the end product in better yields as small amounts of water can have a significant effect on the crystallisation of the salt.

The use of vacuum lowers the azeotropic boiling point for water/n-butanol mixtures. The amount of water removed is also increased which reduces processing time. Thus the use of vacuum speeds up the removal of water and the control of temperature limits impurity formation.

According to a second aspect of the invention there is provided a salt of a substituted or unsubstituted methylene bisphosphonic acid of formula I wherein $X^1$ and $X^2$ are independently hydrogen or halogen. Preferably $X^1$ and $X^2$ are both hydrogen, fluorine, chlorine or bromine, most preferably $X^1$ and $X^2$ are both chlorine. Alternatively, one of $X^1$ and $X^2$ is hydrogen and one is chlorine.

The salt may be a $C_{1-6}$ straight or branched primary, secondary or tertiary alkyl amine salt, an aralkly amine salt, a basic N-containing heterocycle salt, an alkali or alkaline earth metal salt.

Preferably the salt is a $C_{1-4}$ straight or branched primary, secondary or tertiary alkylamine salt an aralkyl amine salt, a basic N-containing heterocycle salt or an alkali metal salt such as sodium or potassium salt.

Most preferably the salt is a triethylamine, tri-n-propylamine, diisopropylethylamine, tri-n-butylamine, pyridine, tribenzylamine or sodium salt. The sodium salt may be the di-, tri- or tetrasodium salt.

The process of the invention will be described in more detail by way of reference to the following non-limiting examples:

EXAMPLE 1

Preparation of Dichloromethylene Bisphosphonic Acid, Mono(tri-n-butylamine) Salt Dichloromethylene bisphosphonate tetraisopropyl ester (10 g. 0.024 mole) was dissolved in 18% hydrochloric acid (30 ml). The resultant solution was added dropwise to a stirred heated (85° C.) solution of 18% hydrochloric acid (10 ml). The solution was then stirred at 85° C. for 2 hours under a flow of nitrogen whilst collecting the distillate (isopropyl chloride). After this time the temperature was raised and the acid distilled off until the minimum volume was reached (5 ml for this experiment). Put and take with water was done keeping the volume as low as possible (13×3 ml portion). The reaction mixture was then cooled prior to the addition of n-butanol (20 ml). Vacuum was applied to the vessel and the temperature raised to remove the water/n-butaniol, keeping the temperature below 100° C. Solvent was again removed until the minimum volume was reached. This was repeated by the addition of two further portions of n-butanol (20 ml). The solution was then diluted with n-butanol to give the product in a total volume of 41 ml. To this solution was added ethanol (9 ml) to give the product at a concentration of 6 ml/g in 15% ethanol/n-butanol. The reaction mixture was then treated with tri-n-butylamine (1.0 equiv.). The reaction mixture was stirred overnight. The suspension was then filtered and the solid washed with n-butanol (3 ml). The damp solid was dried in vacuo at 80° C. overnight to give dichloromethylene bisphosphonic acid, mono(tri-n-butylamine)salt as a white solid in excellent yield (9.27 g, 89%).

| Elemental Analysis | C | H | N |
| --- | --- | --- | --- |
| Calc. % | 36.29 | 7.26 | 3.26 |
| Found % | 36.43 | 7.38 | 3.24 |

EXAMPLE 2

Preparation of Dichloromethylene Bisphosphonic Acid, Monopyridine Salt

To 15.3 ml of an n-butanol solution of dichloromethylene bisphosphonic acid prepared as in Example 1 was added industrial methylated spirits (IMS) (2.7 ml) and the solution was stirred for 5 minutes before the addition of pyridine (0.59 ml. 1.0 eq) which caused instant precipitation. The resultant slurry was stirred overnight. The solid was filtered off and washed with a small amount of n-butanol. The damp solid (2.27 g) was dried in in vacuo overnight at 80° C. This gave the monopyridine salt (2.07 g, 88%).

| Elemental Analysis | C | H | N | |
| --- | --- | --- | --- | --- |
| Calc. %: | 22.24 | 2.80 | 4.32 | $H_2O$, 0.00% |
| Found %: | 22.07 | 2.85 | 4.19 | |

EXAMPLE 3

Preparation of Dichloromethylene Bisphosphonic Acid, Mono(triethylamine) Salt

To 15.3 ml of an n-butanol solution of dichloromethylene bisphosphonic acid prepared as in Example 1 was added n-butanol (2.7 ml) and the solution was stirred for 5 minutes before the addition of triethylamine (1.01 ml. 1.0 eq) which caused instant precipitation. The resultant slurry was stirred overnight. The solid was filtered off and washed with a small amount of n-butanol. The damp solid (2.38 g) was dried in vacuo overnight at 80° C. This gave the mono(triethylamine) salt (2.28 g. 91%).

| Elemental Analysis | C | H | N | |
| --- | --- | --- | --- | --- |
| Calc. %: | 24.29 | 5.53 | 4.05 | $H_2O$, 0.00% |
| Found %: | 24.32 | 5.53 | 3.82 | |

EXAMPLE 4

Preparation of Dichloromethylene Bisphosphonic Acid, Mono(diisopropylethylamine) Salt To 15.3 ml of an n-butanol solution of dichloromethylene bisphosphonic acid prepared as in Example 1 was added IMS (2.7 ml) and the solution was stirred for 5 minutes before the addition of diisopropylethylamine (1.27 ml, 1.0 eq) which caused instant precipitation. The resultant slurry was stirred overnight. The solid was filtered off and washed with a small amount of n-butanol. The damp solid (2.59 g) was dried in vacuo overnight at 80° C. This gave the mono(diisopropylethylamine)salt (2.47 g 91%).

| Elemental Analysis | C | H | N | |
|---|---|---|---|---|
| Calc. %: | 28.29 | 6.20 | 3.74 | $H_2O$, 0.00% |
| Found %: | 28.64 | 6.13 | 3.92 | |

EXAMPLE 5

Preparation of Dichloromethylene Bisphosphonic Acid, Mono(tribenzylamine)salt

To 15.3 ml of an n-butanol solution of dichloromethylene bisphosphonic acid prepared as in Example 1 was added n-butanol (2.7 ml) and the solution was stirred for 5 minutes before the addition of tribenzylamine (2.09 g, 1.0 eq). The resultant slurry was stirred overnight. The solid was filtered off and washed with a small amount of n-butanol. The damp solid (4.35 g) was dried in vacuo overnight at 80° C. This gave the mono(tribenzylamine)salt (3.54 g 92%).

| Elemental Analysis | C | H | N | |
|---|---|---|---|---|
| Calc. %: | 49.64 | 4.73 | 2.63 | $H_2O$, 0.00% |
| Found %: | 49.61 | 4.71 | 2.59 | |

EXAMPLE 6

Preparation of Dichloromethylene Bisphosphonic Acid, Mono(tri-n-propylamine) Salt To 15.3 ml of an n-butanol solution of dichloromethylene bisphosphonic acid prepared as in Example 1 was added n-butanol (2.7 ml) and the solution was stirred for 5 minutes before the addition of tri-n-propylamine (1.38 ml, 1.0 eq) which caused instant precipitation. The resultant slurry was stirred overnight. The solid was filtered off and washed with a small amount of n-butanol. The damp solid (3.28 g) was dried in vacuo overnight at 80° C. This gave the mono(tri-n-propylamine)salt (2.50 g. 89%).

| Elemental Analysis | C | H | N | |
|---|---|---|---|---|
| Calc. %: | 30.94 | 6.49 | 3.01 | $H_2O$, 0.00% |
| Found %: | 31.14 | 6.56 | 3.37 | |

EXAMPLE 7

Preparation of Dichloromethylene Bisphosphonic Acid, Disodium Salt

To 15.3 ml of an n-butanol solution of dichloromethylene bisphosphonic acid prepared as in Example 1 was added a solution of sodium hydroxide (0.58 g. 2 equiv.) in water (1 ml) which caused instant precipitation. The resultant slurry was stirred overnight. The solid was filtered off and washed with a small amount of n-butanol. The damp solid (2.94 g) was dried in vacuo overnight at 80° C. This gave the disodium salt (1.82 g. 87%).

| Elemental Analysis | C | H | |
|---|---|---|---|
| Calc. %: | 4.16 | 0.70 | $H_2O$, 0.00% |
| Found %: | 3.99 | 0.90 | |

What is claimed is:

1. A process for preparing salts of a substituted or unsubstituted methylene bisphosphonic acid of formula I

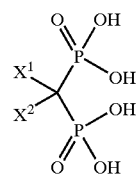

(I)

wherein $X^1$ and $X^2$ are independently hydrogen or halogen, which process comprises hydrolysing, using hydrochloric acid, the corresponding ester of formula II,

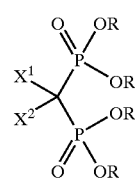

(II)

wherein $X^1$ and $X^2$ are defined above and R is a $C_{1-4}$ straight or branched chain alkyl group and converting the acid to a salt by reaction with a base characterized in that the concentration of hydrochloric acid is from 15% to 20% by weight and water is removed azeotropically from the resultant bisphosphonic acids, using n-butanol, prior to the addition of the base.

2. The process as claimed in claim 1 wherein $X^1$ and $X^2$ are both fluorine, chlorine or bromine.

3. The process as claimed in claim 2 wherein $X^1$ and $X^2$ are both chlorine.

4. The process as claimed in claim 1 wherein the tetraester of formula II is the tetraisopropyl ester.

5. The process as claimed in claim 1 wherein the compound of formula II is dichloromethylene bisphosphonate tetraisopropyl ester.

6. The process as claimed in claim 1 wherein the acid product of the hydrolysis is reacted with an organic or inorganic base.

7. The process as claimed in claim 6 wherein the base is selected from the group comprising $C_{1-4}$ straight or branched primary, secondary or tertiary alkylamine, aralkyl amine, basic N-containing heterocycle or alkali metal hydroxides.

8. The process as claimed in claim 7, wherein the base is selected from the group comprising triethylamine, tri-n-propylamine, diisopropylethylamine, tri-n-butylamine, pyridine, tribenzylamine and sodium hydroxide.

9. The process as claimed in claim 8, wherein the volume of hydrochloric acid used is from about 3 to about 5 volumes of the volume of the hydrolysis reactants.

10. The process as claimed in claim 1 wherein the hydrolysis is carried out at from about 80° C. to about 90° C.

11. The process as claimed in claim 1 wherein a vacuum is applied following the addition of n-butanol.

12. A salt which is selected from dichloromethylene bisphosphonic acid, monopyridine salt dichloromethylene bisphosphonic acid, mono(triethylamine)salt dichloromethylene bisphosphonic acid, mono(diisopropylethylamine)salt dichloromethylene bisphosphonic acid, mono(tribenzylamine)salt dichloromethylene bisphosphonic acid, mono(tri-n-propylamine)salt.

13. The process as claimed in claim 6 wherein the base is $C_{1-6}$ straight or branched primary, secondary or tertiary alkylamine, aralkylamine, basic N-containing heterocycle, alkali or alkaline earth metal hydroxide.

* * * * *